United States Patent [19]

Delnon

[11] Patent Number: 4,694,478
[45] Date of Patent: Sep. 15, 1987

[54] APPARATUS FOR ORTHORADIAL PANORAMIC TOMOGRAPHY

[76] Inventor: Hanspeter Delnon, Seestrasse 24, 8712 Stäfa, Switzerland

[21] Appl. No.: 812,286

[22] Filed: Dec. 23, 1985

[30] Foreign Application Priority Data

Jan. 25, 1985 [CH] Switzerland ............................ 347/85

[51] Int. Cl.[4] ...................... H05G 1/60; G03B 23/04; A61B 6/04
[52] U.S. Cl. ...................................... 378/39; 378/38; 378/180; 378/196; 378/170
[58] Field of Search .................... 378/177, 39, 38, 180, 378/196, 179, 40, 163, 168, 170, 195; 33/515

[56] References Cited

U.S. PATENT DOCUMENTS

| | | | |
|---|---|---|---|
| 2,353,969 | 7/1944 | Powers | 378/177 |
| 3,514,606 | 5/1967 | Rabey | 378/180 |
| 4,599,739 | 7/1986 | Nishikawa et al. | 378/39 |

Primary Examiner—Carolyn E. Fields
Assistant Examiner—Joseph A. Hynds
Attorney, Agent, or Firm—Werner W. Kleeman

[57] ABSTRACT

An apparatus for orthoradial panoramic tomography comprises a radiation source for motion relative to a point of reference; a cassette means also for motion relative to said point of reference; a support for holding said radiation source and said cassette relative to said point of reference; a head positioning means including a first or intraoral device and a second or extraoral device for positioning the patient's head relative to said point of reference; a carriage connected with said support 11 and including a grip; a substantially vertical column for slidingly holding said carriage in a vertically defined position and having a vertical axis distanced from said point of reference; the apparatus further comprises a foot positioning means having a substantially horizontal reference face for defining a vertical distance from said horizontal reference face to said point of reference and a substantially vertical reference face for maintaining toe and/or heel portions of the patient's feet in a predetermined position; a distancing means is provided for maintaining said at least one vertical reference face at a reproducible horizontal distance from said vertical axis of said column; and means is arranged for determining and reproducibly setting a vertical distance between said horizontal reference face and said point of reference; said foot positioning means is arranged relative to said point of reference and to said vertical column axis for maintaining said patient, when standing on said foot positioning means and engaging said gip, in a reproducible and inclined position in which his longitudinal body axis relative to said vertical column axis is at an angle ($\alpha$) sufficient to cause an isotonic strain of brachial and dorsal muscles.

16 Claims, 10 Drawing Figures

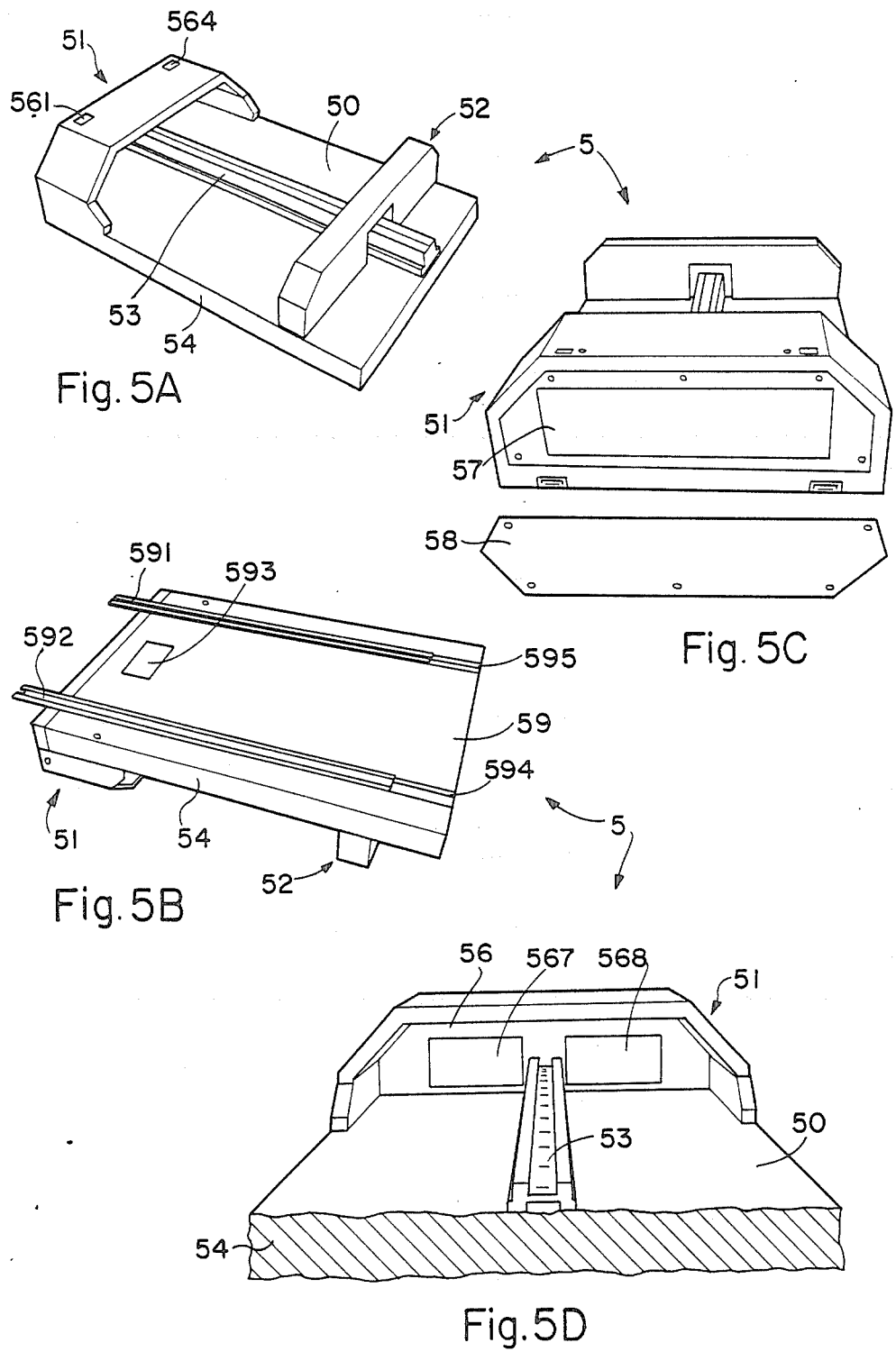

APPARATUS FOR ORTHORADIAL PANORAMIC TOMOGRAPHY

BACKGROUND OF THE INVENTION (a) Field of the Invention

This invention relates to radiography and specifically to an apparatus for orthoradial panoramic tomography.

(b) Description of the Prior Art

Orthoradial panoramic tomography also termed orthopantomography (herein called OPT-technique for short) is a known X-ray method developed and described by Y. V. Paatero since about 1960 for radiographing curved surfaces, most frequently the entire tooth-bearing area of both the upper and the lower jaw, to obtain a sharp and well defined yet flat image, photograph or other type of repreducible record, the orthoradial pantomogram also termed orthopantomogram (herein called OPT for short).

For taking an OPT of the dental or another curved portion of a human patient's head region the entire part, e.g. dentition and adjacent mandibular areas, of interest must be penetrated perpendicularly by a narrow X-ray beam passing from a radiation source to a receptor or film that is sensitive to, and indicative of, X-rays in the radiological wave length.

While pantomography can be made with a stationary apparatus and a moving object, OPT-technique uses an apparatus where both the X-ray source and the film are moved; the film, in turn, is held in a predetermined and generally curved configuration within an enclosure or cassette which, in general, is moved by secondary motion; depending upon the shape of the area or stratum of radiological interest for the particular OPT, X-ray source and cassette means will each move along a more or less complex path around the immobile head of the patient. For example, in order to take a concentric pantomogram of a cylindrical object or plane one would rotate both the X-ray source and the film cassette carrier around a single common axis of rotation which, in turn, would coincide with the axis of the cylindrical object while the cassette is also moved relative to the cassette support.

However, since typical objects of interest, such as the jaws, are not cylindrical, sharp X-ray imaging may require that the X-ray source and the cassette are moved along a particular path each involving more than one, say three or an infinite number of axes of rotation, i.e. a more or less continuously shifting position of the common axis of rotation; in other words, orthoradial pantomography of a noncylindric layer or stratum requires an excentric pantomogram including other than circular motion of the X-ray source and/or the cassette support. Numerous detailed studies about optimizing such motion for specific OPT purpose can be found in the literature, cf. Acta Orthodontica 13 (1985) 445–453.

While the particular type of movement of X-ray source and cassette or film support is not believed to be essential for the present purpose, the coordinated movement must be definitive, i.e. fully defined and reproducible and relation to an arbitrary, yet fixed, point of reference generally assumed to be positioned in a vertical plane of symmetry of the object of interest and/or the apparatus which plane, in turn, preferably will coincide with the mediosagittal plane of the patient when the OPT is taken.

For convenience and simplicity, such point is assumed herein to be located at a fixed, or fixable, point of the apparatus such that the point of reference will be within the oral cavity of the patient when an OPT is taken with the apparatus.

Another requirement for the present apparatus is that the OPT can be taken of a patient in "erect position", i.e. standing on his feet as opposed to sitting or lying; from this further requirement it will be apparent that the predetermined motion of each the radiation source and the cassette means will be in an essentially horizontal plane, i.e. intersecting perpendicularly with the standing patient's head axis in the mediosagittal plane.

OPT-apparatus meeting these requirements are available commercially from various sources; illustrative apparatus examples will be given below.

Detailed explanations of prior art OPT-apparatus will be found in the literature, e.g. U.S. Pat. No. 3,673,408 (issued June 27, 1972) and U.K. Pat. No. 2,006,590 (published May 2, 1979); such apparatus may include head positioning means comprising separate devices for the upper head portion and the lower head portion so that the patient's head can be positioned relative to the above-defined point of reference so as to obtain reasonably well-defined OPTs. However, even with the most stringent prior art head positioning devices (intraoral support or "bit" structure combined with extracranial points of contact so as to align the vertical axis of the patient's head) the OPTs, while sharp in the area of interest, are not fully reproducible, that is, "congruent" to the extent that a first and a subsequent OPT taken some time after the other could be mutually superimposed and then match in all those portions that have not changed since the first OPT was taken. In fact, the degree of reproducibility reported in the clinical studies that were discussed in the above-mentioned review by Marxer, H. in Acta Orthodontica was not sufficient to permit comparative measurements as pointed out by that author.

For diagnostic purposes, i.e. to determine time-dependent changes in a patient's head region, such as tumor diagnosis, control and treatment of undesirable dental changes and the like purposes, it would be extremely desirable to provide for congruent OPTs in the sense defined above, i.e. permitting measurements of time-dependent changes because unchanged portions would be apparent as reference positions from congruent OPTs.

The research leading to the present invention has shown that reliable congruence of sequential OPTs cannot be achieved safely with prior art apparatus even if the patient does not leave the apparatus at all and even if the time span between the first OPT and a sequential OPT is but a few minutes, not to speak of congruence of OPTs after time intervals of weeks, months or even years between the first (or preceding) and a second (or subsequent) OPT.

OBJECTS AND SUMMARY OF THE INVENTION

Accordingly, it is a main object of the invention to provide for an OPT apparatus that is capable of yielding congruent OPTs, even after passage of a time interval in the range of several weeks or months between a first or preceding OPT and a subsequent OPT as would be typical for normal observation intervals in a given medical field.

A further object of the invention is to provide for an apparatus which allows congruent OPTs having a degree of congruence (expressed as linear divergence) of better than about ±1% between a preceding and a subsequent OPT with a time lapse in the order of several weeks or months and probably up to some years (based on present experience).

Another object of the invention is to provide for an apparatus that is capable of producing congruent OPTs with a structure that requires neither substantial sophistication above that of prior art OPT-apparatus, nor a substantial increase in apparatus costs.

Yet a further object of the invention is to provide for an apparatus capable of producing congruent OPTs with an essentially minor structural variation of presently available OPT-apparatus.

Further objects of the invention will become apparent as the specification proceeds.

Generally, I have found that even the most accurate positioning of merely the patient's head relative to the point of reference is not sufficient for congruent OPTs and that the apparatus used must co-act with a body portion substantially remote from the head so as to achieve a patient's position that is not only reproducible but, additionally, causes what can be termed a "muscularly induced body rigor" lasting for the normal time of OPT-exposure typically from a few seconds to half a minute, and being of the type caused intentionally by a patient who stands erect and is instructed to hold himself by his hands on a defined grip while his feet are positioned in a forward direction in the apparatus such that the patient's center of gravity is posterior to his heels. In other words, the OPT-apparatus must be modified such that it causes the patient to produce "body rigor" effective to immobilize his vertebra by isotonically straining his brachial and dorsal muscles to the extent required for maintaining a reproducible backward inclination. Generally, the apparatus should cause that the patient's occipital joint will be in a reproducible position during OPT-exposure as well and permit maintaining the vertical head axis at an angle of from about 175° to about 150° relative to the inclined longitudinal body axis; in other words, the plane of mastication of the patient should be substantially horizontal even though the body axis is held in inclined position.

Specifically, I have found that the above objects and further advantages will be achieved, according to the invention, by means of an apparatus for orthoradial panoramic tomography of a head region (term used herein to include any cranial, facial, oral, nasal, foraminal or cervico-vertebral area of radiological interest in addition to the dental area of prime importance) of a human patient in an erect position defined essentially by a longitudinal body axis when the apparatus comprises:

(a) a radiation source arranged for predetermined motion, generally in an essentially horizontal plane relative to a point of reference (as defined above);

(b) a cassette means (generally including a film, an enclosure or cassette and a cassette support) for selective exposure of a film sensitive to X-ray radiation from the radiation source, said cassette means also being arranged for predetermined motion, generally in an essentially horizontal plane relative to the point of reference;

(c) a means for movably supporting the radiation source and the cassette means relative to the point of reference;

(d) a head positioning means including first and second devices for positioning the patient's head relative to the point of reference;

(e) a carriage connected with the support means and including a grip;

(f) a substantially vertical column for holding the carriage in a vertically defined position and having a vertical axis ($A^1$) distanced from said point of reference, and for slidingly displacing the carriage in a vertical direction, and when the apparatus additionally is provided with:

(g) a foot positioning means having a substantially horizontal reference face for defining a vertical distance between the patient's foot soles (planta pedis) and the point of reference, and a substantially vertical reference face for maintaining toe and/or heel portions of the patient's feet in a predetermined position;

(h) a distancing means for maintaining the vertical reference face at a reproducible horizontal distance from the vertical axis of column (f);

(i) a means for determining and reproducibly setting a vertical distance between the horizontal reference face and the point of reference; and wherein the foot positioning means (g) is arranged relative to the point of reference and to the vertical column axis ($A^1$) for maintaining the patient, when standing on the foot positioning means and engaging said grip, in a reproducibly inclined position in which his longitudinal body axis ($A^2$) relative to the vertical column axis ($A^1$) is at an angle ($\alpha$) that will cause an isotonic strain of brachial and dorsal muscles of the patient while engaging said grip means, preferably at an angle ($\alpha$) of between 5° and 30°, more preferably between 15° and 25° and, typically, at about 20°.

It will be understood that the use of foot positioning means or "foot plates" has been known, per se, in radiology for many years, e.g. in the distortion apparatus of U.S. Pat. No. 3,256,611 (issued 1966), or as an optional body support for the X-ray machine of U.S. Pat. No. 3,514,606 (issued 1970).

However, as the hitherto unsuccessful search for means and ways of obtaining congruent OPTs would seem to indicate, it was not to be expected that such a relatively simple means in proper arrangement as a complement would be sufficient to resolve the problem.

As regards the foot positioning means of the inventive apparatus it will be understood that the substantially horizontal reference face of the foot positioning means (g) preferably is a structural surface of a foot positioning plate suitable to support, without significant deformation, the weight of a patient standing thereon; by the same token, the substantially vertical reference face preferably is a stationary wall portion of such a foot plate and, generally, will intersect perpendicularly with the mediosagittal plane of the patient.

The distancing means (i) can be a discrete element, such as a securing device, that holds the foot positioning means, or plate, at a reproducible distance from the vertical axis of column (f); alternatively, the distancing means is an integral part of the foot plate, e.g. a stop-surface or plate for abutting and/or locking engagement with column (f).

Further, according to a generally preferred embodiment, the foot positioning means according to the invention includes at least one longitudinal reference face, i.e. "longitudinal" in the sense of extending in the direction from the axis of column (f) to a vertical projection of the point of reference onto the plane which extends through the horizontal reference face or parallel to such direction.

The longitudinal reference face or, preferably, a pair of parallel longitudinal reference faces is intended for positioning the patient's feet at mutually equidistanced positions relative to a vertical plane defined by the point of reference and the vertical axis of column (f); further, such vertical plane should be essentially coplanar with the mediosagittal plane of the erect patient when the OPT is taken; also the longitudinal body axis of the patient should essentially be in that plane when the OPT is taken.

Generally, the preferred positioning plate has a straight longitudinal ridge for contact with the adjacent "inner" sides (i.e. those next to the mediosagittal plane) of the patient's feet.

That ridge may further serve as a rail or guide for a second and movable vertical face, e.g. a transverse plate, that can be positioned in contact with both heels of the patient's feet after the same have been brought into contact with the stationary vertical face or surface that is in contact with the toe portions of both feet of the patient.

It will be understood that the term "in contact with" the toes of the patient's feet means that type of contact that occurs when a patient is positioned so that the most prominent toe portion of each of his feet is in contact with a vertical plane which, in turn, is perpendicular to the mediosagittal plane of the erect patient.

Further, it should be noted in this context that it is not believed to be essential whether the foot position of the patient in the OPT-apparatus according to the invention is defined but by the toe position, or by the heel position, or both, of the patient's feet.

For practical reasons, the foot positioning means (g) of the inventive apparatus comprises the vertical reference face as a stationary surface for contact with the patient's toes while a second adjustable vertical surface substantially parallel with the reference face is for contact with the patient's heels.

Pressure sensors may be used to ascertain contact or achievement of a predetermined contact pressure as explained below.

From the requirement that the inventive apparatus is capable of positioning the patient's feet in the manner needed to cause the inclined body position explained above and to do so in a reproducible manner, it will be understood that the point of reference should be in a fixed position relative to the carriage means as is conventional for commercially available OPT-apparatus. Thus, in order to determine, or reproducingly set, the vertical distance between the horizontal reference face of the foot positioning means (g) and the point of reference, the distancing means (i) provided for this purpose may be any conventional device for measuring a distance, e.g. a scale mounted on column (f) for cooperation with a marker mounted on carriage (e); mechanical or non-mechanical means to determine a distance and indicating it, e.g. in terms of a digital value, or to reset a previously determined distance may be used.

Here, it will be understood that the term "vertical distance" between the point of reference and the horizontal reference face of the foot positioning means (g) refers to the distance between the plane defined by the horizontal reference face and a plane parallel thereto extending through the point of reference. For convenience, the point of reference may be conceived as a "determinative site" of the bit structure which, in turn, is held in a defined spatial relation to carriage (e) explained below in more detail.

Head positioning means comprise a first or intraoral (i. e. in contact with a region within the oral cavity) and a second or extraoral positioning device. Combinations of intraoral and extraoral positioning means are known in radiology, e.g. from U.S. Pat. No. 3,514,606, and aim at optimum definition of the position of a patient's head.

Now, while even the best prior art head positioning means will not, per se, be capable to yield congruent OPTs, use of such best means is preferred in the inventive apparatus; such best means include a bit structure made of a rigid yet radiologically transparent material and mounted in a fixed, or reproducibly adjustable or reproducibly exchangeable, manner or carriage (e) combined with a three-point, external head positioning device of the type disclosed in the above mentioned U.K. specification (GB No. 2,006 590) and also being connected in a spatially defined manner with carriage (e).

Commercially available OPT-apparatus may have such positioning means, or may be fitted therewith.

For simplicity of illustration it will be assumed herein that the point of reference mentioned above for definition of the foot positioning means and its function as part of the inventive apparatus can be a discrete (and visible) point on the bit structure even though the "theoretical" point of reference may be at a different point in space relative to the carriage means. This will be understood from the above explained view-point of congruence of sequential OPTs and the fact that a reproducible definition of the spatial relation of the patient's head relative to each and every position of both radiation source (a) and cassette means (b) while an OPT is taken is a necessary but not a sufficient condition that must be achieved with the inventive OPT-apparatus (which, additionally defines a specific foot position).

Consequently, the actual location of the point of reference is not essential as long as its relation to a "determinative site" (point, line or surface) is defined and reproducible.

It has been found that is such "determinative site" is at an upper portion of the intraoral positioning means or bite structure, congruent OPTs can be obtained with the inventive apparatus but since OPTs may be required both for patients with substantially complete or with substantially missing dentition, the inventive apparatus provides for different bite structures: the first type will be called a "tooth-engaging" structure and used for patients that have all or most incisors; the second type will be called "gum-engaging" structure and used for patients where all or most incisors are missing.

The term "gum" is used herein to refer to the firm tissues in the upper and lower jaw in which teeth, if present, would be set, and which remain when teeth are lost or extracted; most OPTs can be taken with tooth-engaging structures of the type known per se since most patients will have native or prosthetic incisors.

Such prior art structures may have the general shape of an inversed "L" or "cobra head" such that the longer leg or cobra neck serves for rigid connection with a holder or socket of carriage (e) while the shorter leg or cobra nose is a small block with at least one short groove at its upper surface for receiving a common edge portion of the frontal incisors; a traverse marker line may indicate a center site as "determinative site"; the lower block surface may, and preferably does, carry another short groove for engagement with edge portions of the lower frontal incisors.

In some cases, e.g. for extensive dental repair such as after an accident, a novel bite structure of the gum-engaging type will be required as explained in more detail below; such structures may be standardized or tailor-made as required and a determination site at the upper side of the bit structure may be marked.

Hybrid bite structures may be provided if needed, e.g. having a gum-engaging upper (or lower) and a tooth-engaging lower (or upper) side if required and would be tailormade, e.g. by conventional dental molding techniques.

In tooth-engaging and/or gum-engaging bite structures opposed (i.e. at opposite sides of the mastication plane) jaw portions of the patient will be in contact with the bite structure.

Carriage means (e) with grip means, e.g. a rail member, a pair of handles or the like elements, positioned at the lower side of the carriage structure may further include self-positioning controls that help the patient to find a centered position of the head after positioning of the feet; such controls may include a mirror in the field of vision of the patient provided with crosswebs. Further, a lower edge portion of carriage (e) may serve as a stop means for contact with a sternal portion of the patient and/or have a protrusion for contact with a clavicular portion of the patient.

BRIEF DESCRIPTION OF THE DRAWINGS

The invention will be better understood and objects other than those set forth above will become apparent when consideration is given to the following detailed description. Such description makes reference to the annexed drawings which illustrate exemplary embodiments of the apparatus according to the invention and of particular features of such apparatus and wherein

FIGS. 5A, 5B, 5C and 5D are perspective views of a preferred foot positioning plate for use with an apparatus of the type shown in FIG. 1.

DETAILED DESCRIPTION OF PREFERRED EMBODIMENTS

Figure 1:
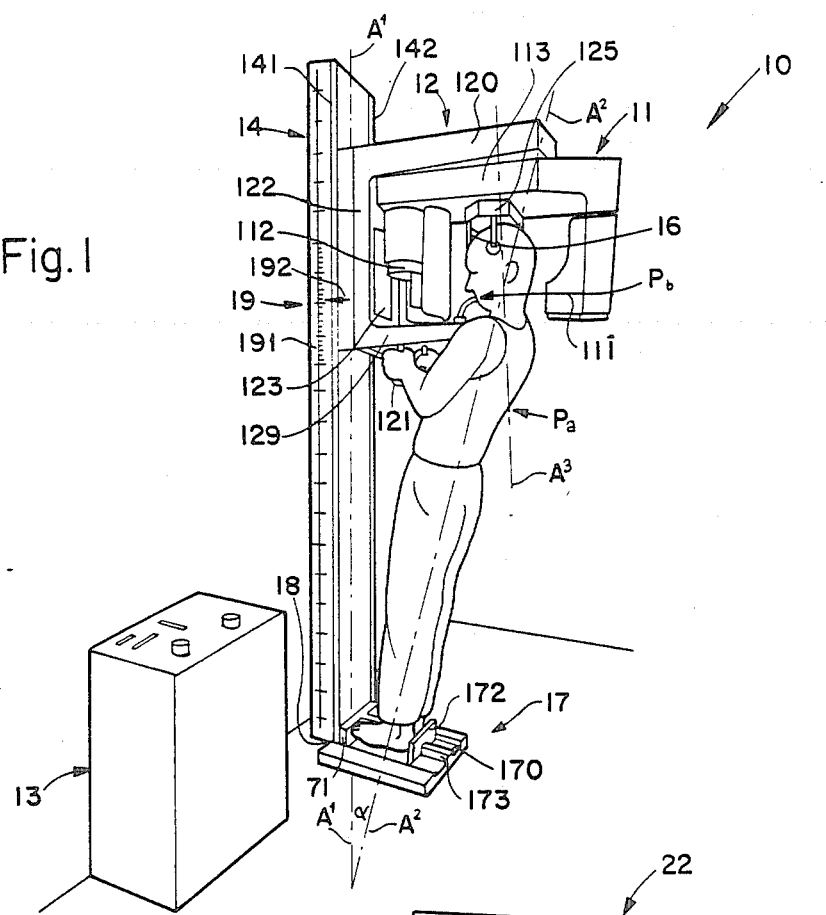
FIG. 1 is a perspective view of an apparatus according to the invention with a patient positioned therein for taking congruent OPTs.
Figure 2:
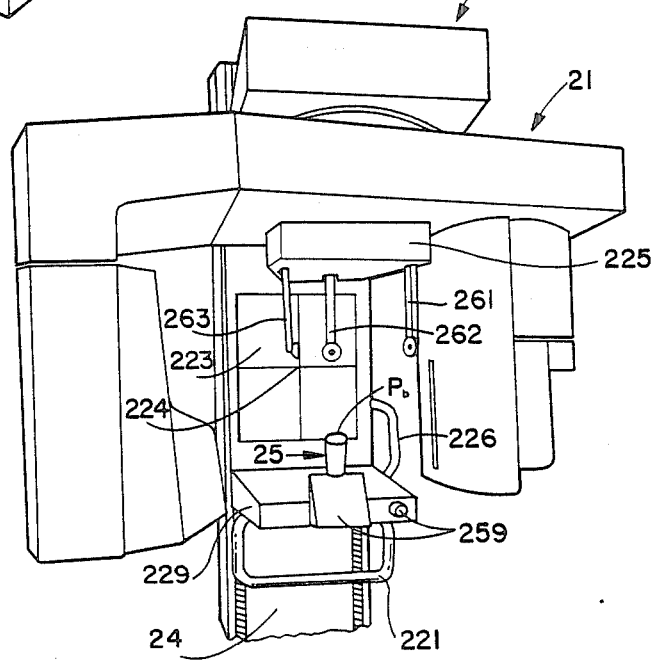
FIG. 2 is a somewhat enlarged perspective view of the upper part of the apparatus of FIG. 1 shown without the patient and with the support structure turned to show details.

The apparatus 10 depicted in FIG. 1 includes the portions of commercially available OPT apparatus, e.g. as manufactured by Philips, Holland, and sold under the trademark "orthoORALIX", or a comparable apparatus sold by Siemens, Germany; it will be understood, however, that no restriction to a particular type of OPT apparatus is intended except that it must have the following features:

(a) an X-ray source 111 of conventional structure for predetermined motion (drive not shown) relative to a point of reference Pb positioned intraorally in the patient's mouth as shown in FIG. 1 and seen best in FIG. 1 at the upper surface of bite structure 25;

(b) a cassette means 112 of conventional design for selective exposure of an X-ray film (not depicted) to radiation from source 111 including a curved cassette for enclosing the film and a securing means for connecting the cassette with a cassette support (drive not shown);

(c) a conventional support means 113 for holding the X-ray source 111 and the cassette means 112 relative to reference point Pb such that they can be moved in accordance with a predetermined program suited for the specific OPT purpose, here taking of a dental OPT in horizontal planes around the patient's head. To this effect, support means 113 forms a composite radiographic structure 11 together with the X-ray source 111 and the cassette means 112; structure 11 is rotatably connected with the upper arm or bracket 120 of carriage means 12. Conventional light beam sources (not shown) may be provided for overall positioning;

(d) conventional head positioning means comprised of an intraoral positioning device 25 (within patient's oral cavity, not apparent from FIG. 1 but shownin FIG. 2) mounted on the lower arm or bracket 129 of carriage 12, and an extraoral head positioning device 16 (comprised of three adjustable contact arms 261, 262, 263 as shown in FIG. 2) mounted on head plate 125 (225, FIG. 2) which, in turn, is connected rigidly with the upper arm 120 of carriage means 12 (FIG. 2: 22);

(e) a conventional carriage means 12 consisting of the upper arm 120, the lower arm 129 and the connecting portion 122, in addition to rotatably holding support 113 includes a grip 121 (FIG. 2: 221), e.g. a rail or bar secured to the lower arm 129;

(f) a conventional and substantially vertical column 14 provided for holding carriage means 12 such that the latter can be held in a vertically defined position, e.g. as shown in FIG. 1 or with a smaller or larger patient in a lower or higher position. The vertical axis of column 14 is a theoretical line $A^1$ assumed to be located in the vertical plane that is defined by reference point Pb.

As shown in FIG. 1, column 14 may support carriage 12 in a conventional manner via two slits 141, 142 by means of connectors (not shown) for sliding engagement with a shaft or group of shafts (not shown) within column 14, and conventional mechanical or pneumatic devices (not shown) will normally be provided to balance the weight of carriage 12 and those components of apparatus 10 that are supported by the carriage and to provide for easy movement of carriage 12 in vertical directions.

According to the invention a foot positioning means is provided, e.g. in the form of a plate 17, having a top surface 170 upon which the patient places his bare feet and which is in a defined vertical distance from reference point Pb (as measured between a horizontal plane through Pb and the horizontal plane defined by surface 170).

A stationary vertical front plate 171 is in contact with patient's toes as shown in FIG. 1 while the heels are in contact with a vertical back plate 172 that is guided by a longitudinal ridge or rail 173 which also contacts the inner sides of patient's feet so as to define their longitudinal orientation.

A distancing means 18 is required to define the distance between the vertical reference face provided in FIG. 1 by the toe-contacting surface of the stationary vertical plate 171, and axis $A^1$ of column 14. The actual distance between axis $A^1$ and the vertical reference face is not believed to be overly critical as long as the angle $\alpha$ enclosed between axis $A^1$ of column 14 and the longitudinal body axis $A^2$ of the erect patient is within the range required for muscularly induced body rigor as explained above, and generally within the range of from about 5° to 30° (assuming 360° for a full circle). In the embodiment of FIG. 1 a front portion of foot plate 17 abutting with column 14 serves as fixed distancing means but adjustable distancing means for adaption to smaller or older and less flexible patients are within the scope of the invention and will be explained with reference to FIG. 3.

For determining the vertical distance between surface 170 foot plate 17 and reference point Pb a linear scale 191, e.g. a metric scale reading in millimeters, is provided on column 14 while a marker or arrow 192 is arranged on carriage 12. Other onventional metering or distance reading and setting means including digital read-outs and digital settings may be used for the inventive apparatus. Control and setting means for taking the OPT are provided within console 13.

FIG. 2 shows a somewhat enlarged presentation of the upper part of apparatus 10 of FIG. 1 without the patient and with support 21 turned from the position of 11 in FIG. 1 by a rotation on carriage 22 of about 90°.

Thus, it will be seen that the head plate 125 of FIG. 1 remains stationary (225) so that the pivotably adjustable arms 261, 262 and 263 may hold patient's head in a given position regardless of the position of support 21 because of the rigid connection of the head plate 225 with the top arm of carriage 22; by the same token, the lower arm 229 of carriage 22 maintains bite structure 25 ("cobra-head" type for normal dentition) as well as any body stops 259 and grip 221 in a set relation to the point of reference Pb assumed to be at the center of the top surface of bite structure 25. Sometimes, such arrangements are called "kephalostats" in the art but are not preferred herein if the first device of the head positioning means is a chin support and, thus, not intraoral.

An operating grip 226 may be provided at the side of carriage 22 for lifting or lowering the carriage by the operator and for blocking in or deblocking from a given carriage position.

A mirror 223 including a crosshair 224 is provided on carriage 22 for helping the patient to attain a well centered head position in the course of the positioning sequence explained in more detail below.

Figure 3:
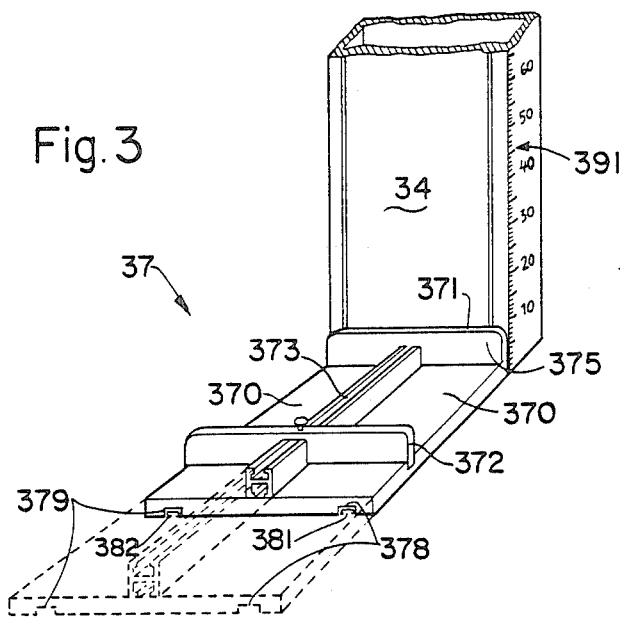
FIG. 3 is a semidiagrammatic view of a foot positioning means mounted at the lower end of the apparatus of FIG. 1, FIGS. 4A, 4B and 4C are perspective view of an intraoral positioning device in the form of a bite structure of the gum-engaging type.

FIG. 3 shows a semi-diagrammatic perspective and enlarged view of the foot plate 17 of FIG. 1 as foot plate 37 with some modifications. The foot of the vertical column 34 for guiding the carriage (not shown) is depicted with a scale 391 for indicating the vertical distance between the horizontal reference face of an inventive apparatus that comprises a foot positioning means (g) in the form of foot plate 37 having a substantially rigid patient-supporting top surface 370 and a stationary vertical plate 371 for contact with the patient's toes. Again, a longitudinal rail or ridge 373 is provided for contact with the inner sides of patient's feet and for guiding the adjustable second vertical plate 372 into contact with patient's heels.

In order to maintain the toe contacting vertical face or surface 375 at a reproducible yet variable distance from column 34 or its vertical axis (not shown in FIG. 3), a pair of rails 381, 382 is provided for sliding engagement with a pair of longitudinal recesses 378, 379 at the bottom side of foot plate 37. Rails 381, 382 will be secured (not shown) to the floor on which column 34 is mounted so that plate 37 may be set to either abut, by means of vertical plate 371, on column 34 or to be maintained at defined distances thereform, e.g. by means of numbered fixed settings (not shown) or the like means that enable an easily reproducible placing of foot plate 37 relative to column 34.

Figures 4A, 4B, 4C:
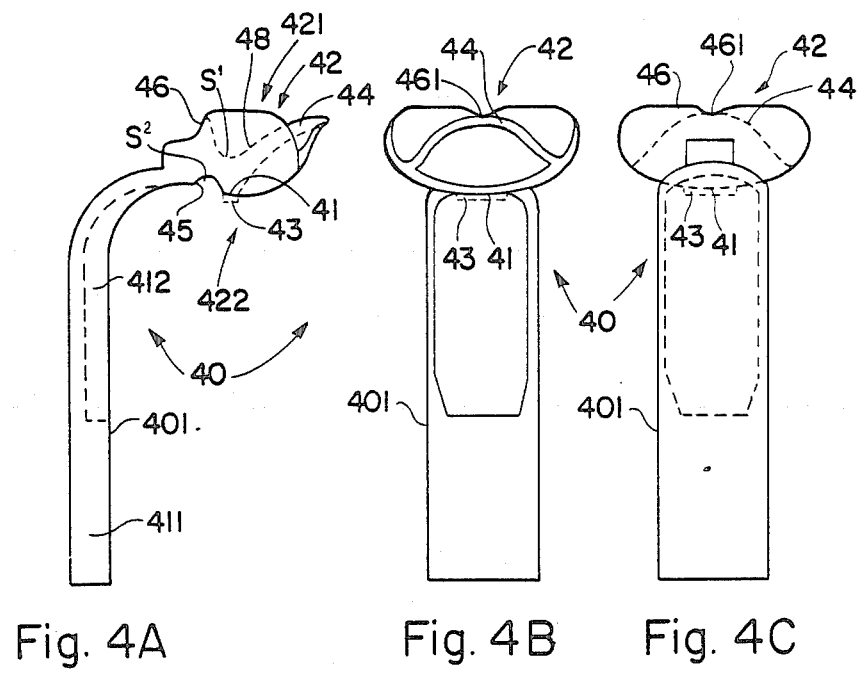

As mentioned above, intraoral positioning devices of the tooth-engaging type suitable for use with the inventive apparatus are known per se while devices of the gum-engaging type for OPT use are believed to be novel in dental radiology. Accordingly, perspective views of a representative example of such a device are shown in FIGS. 4A (side view), 4B (posterior view) and 4C (front view) depicting a bite structure 40 preferably made of an organic polymer that is essentially transparent to X-rays, e.g. a polymethacrylate, polyamide, polycarbonate, epoxy resin or similar physiologically inert thermoplastic or duromeric material capable of being sterilized.

A substantially rigid stem 401 serves for a positionally reproducible connection of bite structure 40 by means of its massive end 411 with a socket or other holder (not shown) of the carriage in a similar manner as is used to position bite structure 25 in carriage 22 of FIG. 2.

The upper part of stem 401 may be provided with a recessed profile 412 providing sufficient rigidity to the connection of the stem with the intraoral support 42 which, in turn, has an upper side 421 and a lower side 422; upper side 421 serves as a palate support and palate positioning device frontally terminating in a stop ridge 46 which has a recess 461 to accomodate the patient's labial band, and comprises a groove smoothly curved (both in vertical and horizontal planes) from stop ridge 46 to palatum support surface 48 and defined by its apex $S^1$ (normally the most frontally located bottom point) which forms the determinative site of bite structure 40; consequently, palatum support wall 44 should be shaped so as to guide and position a toothless (incisors missing) upper jaw into the reproducible spatial relation relative to the carriage means required for congruence of sequential OPTs.

In an analogous manner, lower side 422 of bite structure 40 serves to position the lower (toothless or dented) jaw of the patient into a reproducible position defined essentially by the location of apex $S^2$ of recess or groove 45 that may, or may not, be curved when viewed in a horizontal plane; further, a protrusion base 41 is generally provided and may have a monolithic structure (extending into the portion shown in broken line) or a composite structure in that an exchangeable protrusion or riser 43 (as indicated in broken line) may be added to base 41 so as to adapt the total height of the resulting frontal bite wall to the toothed/untoothed structure of the patient's lower jaw. Generally, apex $S^2$ should be located more frontally, i.e. closer to the vertical axis $A^1$ of the apparatus column, than apex $S^1$.

A preferred embodiment of the foot positioning means 17 of FIG. 1 is shown in various perspective views in FIGS. 5A (operative position), 5B (reversed to show bottom structure), 5C (cover plate of frontal portion removed) and 5D (posterior portion broken away).

Foot positioning means 5 comprises a frontal portion 51 rigidly connected with a massive bottom plate 54 having a flat horizontal top face 50 providing the horizontal reference face explained above.

The vertical reference face 56 (FIG. 5D) includes two (or more) contact faces 567 568 connected via pressure sensitive switches (not shown) with a circuit, e.g. provided on a print plate 57 (FIG. 5C) normally covered by a panel 58.

A battery arranged in a recess 593 is connected by the switches with indicator lights at the top of portion 51 so that one pair of indicator lights, e.g. 562, 563, will indicate that the pressure sensitive switches are energized but not activated, i.e. not in pressing contact with a patient's toes, while another pair of indicator lights, e.g. 561, 564, will indicate that one, some or all of the pressure sensitive switches connected with contact faces 567, 568 are operated by pressure of the patient's toes.

A longitudinal ridge 53 is mounted on the top face 50 of plate 54 and serves both as a rail to guide an adjustable vertical plate 52 in parallel alignment with reference face 56 into contact with both of a patient's heels, and to align the mediosagittal plane of the patient with the vertical plane defined by the center line of ridge 53 and axis $A^1$ of the apparatus column (not shown in FIGS. 5).

Two longitudinal recesses 594, 595 in the bottom face 59 of plate 5 are provided to engage with a pair of rails 591, 592 secured to the floor (not shown) that also supports the vertical column of the apparatus; rails 591, 592 are secured in such manner that the center line of ridge 53 will intersect with the vertical axis $A^1$ of the apparatus column; stopper means (not shown) are provided on rails 591, 592 or on plate 5 to reproducibly and securely define the distance between reference face 56 and axis $A^1$ when an OPT is taken.

Finally, an electrical switch (not shown) will be provided to connect the battery in recess 593 with circuit plate 57.

A step-by-step description will now be given to illustrate the manner of operating an inventive apparatus when taking an OPT that will be congruent with at least one other OPT taken previously or subsequently, i.e. sequentially with an intervening time interval of hours, days, weeks or months;

(1) X-ray-sensitive film is arranged within the cassette in a reproducible manner; film sizes and cassettes are standardized in the sense that same cassettes and film sizes will be used in sequential OPTs. This is the same for all patients.
(2) The cassette is mounted on the cassette support in reproducible if not standard position; this, normally, is the same for all patients.
(3) Position and type of the bite structure are controlled if standard, or selected and mounted in a defined and reproducible manner; identical structures and settings must be used for the same patient.
(4) Position of foot plate, and possibly type of plate, is controlled and, if required, moved into a defined reproducible position if patient's height so requires; longitudinal axis $A^2$ of patient should be at angle $\alpha$ of between 15° and 25°, optimally at about 20°, relative to axis $A^1$ of apparatus column when his toes are in contact with the vertical reference face and an identical setting must be used for all sequential OPTs of the same patient. Other patients may require a smaller angle $\alpha$.
(5) Patient with bare feet is caused to step onto the foot positioning means, e.g. foot plate 5 (FIGS. 5), and— while engaging any grip of the apparatus—places both feet with their inner sides against ridge 53 and moves toes of both feet into contact with faces 567, 568 until control lights indicate that toe contact is established; then plate 52 is moved to contact both heels of the patient, and contact of inner side of patient's feet with ridge 53 is controlled. This operation is the same for all patients except for the position of plate 52.
(6) Patient is caused to engage the grip as high as possible; again, this is the same for all patients.
(7) The apparatus carriage is positioned such that patient is just able to engage the bite structure with his teeth edge to edge while his head is flexed backwards; the patient is now in an erect yet hanging position with a stretched thorax and his longitudinal body axis will be at an angle relative to the axis of the apparatus column, but this angle may exceed that angle ($\alpha$) which is finally desired.
(8) The horizontal line of the crosshairs of the self-positioning control mirror is set along the bi-pupillar line and patient is requested to align his head position.
(9) While patient maintains his body position the apparatus carriage is moved downwards so as to cause a forward pitch of the atlanto occipital joint of the patient and maximum flexion of the cervical vertebra in ventral direction; referring to FIG. 1 of the drawing, the position of axis $A^2$ of patient Ta should be maintained during this operation without change of angle while axis $A^3$ is brought into an essentially vertical position; this results in an optimal elongation of the cervical vertebra and, at the same time, should align patient's plane of mastication parallel with surface 50 of foot plate 5.
(10) The head positioning device, unless already in working position, is set for contact with patient's head; a final check of the head position is made and the setting recorded if variable.
(11) Patient is required to draw his body into contact with the sternal and/or clavicular stop of the carriage and to retain this position; this will cause an isotonic muscular strain of his arm and back muscles; now his body axis $\alpha$ should be at the final value, preferably about 20°.
(12) The vertical level of the carriage is recorded, preferably together with the time of day.
(13) The OPT is taken in accordance with the instructions given by the producer of the OPT-apparatus taking care that all variable settings are recorded for reproduction in sequential OPTs.
(14) Any sequential OPT is made by repeating steps 1 to 13 with identical settings of all variable and, preferably, at about the same time of the day in order to avoid as far as possible different degrees of compression of the vertebra.

Contrary to what has been believed feasible or, rather, impossible in OPT-technique as regards congruence, the invention provides for reproducibility and congruence of sequential OPTs in the sense of true reproduction as evidenced by putting on top of each other two or more sequential OPTs obtained with the inventive apparatus in the manner explained; true reproduction or congruence can be ascertained simply by aligning superimposed OPTs so as to form a composite, or multilayer, OPT in which any unchanged area of one OPT layer is fully congruent and cannot be discriminated visually from the same area of any other OPT in the composite while any lack of congruence, or identical reproduction, indicates actual change of the object.

While actual physical superimposition of congruent OPTs is a preferred method of controlling change in the OPT-area of interest, comparison by projection onto a screen or by electronic scanning and computer evaluation etc. is feasible.

Two further surprising advantages have been observed when taking congruent OPTs with the inventive apparatus: One additional benefit is a remarkable increase of sharp OPT-definition of the anterior bone structure (central area of dental OPTs including frontal jaws plus dental region from canine to canine) where prior art apparatus produce an overprojection in that projection area and require use of another radiological projection, e.g. a posterior/anterior panoramic image of the lower jaw, for complete evaluation.

The second advantage is that the distortion factor of a given OPT-area can be determined reproducibly and used for spatial orientation, e.g. for implantates and target surgery, in a head area of interest.

Generally, the invention may lead to a break-through in maxillo-facial radiology and while preferred embodiments of the present invention were shown and described above, it is to be understood that the invention is not limited to such embodiments but may be embodied and practiced within the scope of the following claims.

Accordingly, what I claim is:

1. An apparatus for orthoradial panoramic tomography of a head region of a human patient in an erect position defined essentially by a longitudinal body axis, said patient having feet including heels and toes; said apparatus comprising:
   (a) a radiation source arranged for predetermined motion relative to a point of reference;
   (b) a cassette means for selective exposure of an X-ray sensitive film to radiation from said source, said cassette means also being arranged for predetermined motion relative to said point of reference;
   (c) a support means for movably holding said radiation source and said cassette means relative to said point of reference;
   (d) a head positioning means including an intraoral device and an extraoral device for positioning said patient's head relative to said point of reference;
   (e) a carriage means connected with said support means and including a grip means;
   (f) a substantially vertical column means for slidingly holding said carriage means in a vertically defined position and having a vertical axis distracted from said point of reference;
   (g) a foot positioning means having a substantially horizontal reference face for defining a vertical distance from said horizontal reference face to said point of reference, and a substantially vertical reference face for maintaining toe and/or heel portions of said patient's feet in a predetermined position;
   (h) a distancing means for maintaining said at least one vertical reference face at a reproducible horizontal distance from said vertical axis of said column means;
   (i) a means for determining and reproducibly setting a vertical distance between said horizontal reference face and said point of reference;
said positioning means being arranged relative to said point of reference and to said vertical column axis for maintaining said patient, when standing on said foot positioning means and engaging said grip means, in a reproducible and inclined position in which his or her longitudinal body axis relative to said vertical column axis is at an angle ($\alpha$) sufficient to cause an isotonic strain of brachial and dorsal muscles.

2. The apparatus of claim 1, wherein said foot positioning means additionally includes at least one longitudinal reference face for positioning said patient's feet in a mutually equidistanced position relative to a vertical plane defined by said point of reference and said vertical axis.

3. The apparatus of claim 1, wherein said column means comprises a scale and wherein said carriage means comprises a marker for determining a reproducible distance between said point of reference and said horizontal reference face of said foot positioning means.

4. The apparatus of claim 1, wherein said vertical reference face or said positioning means includes a stationary surface for contact with both of said patient's toes.

5. The apparatus of claim 1, wherein said foot positioning means further includes an adjustable second vertical face for contact with both of said patient's heels.

6. The apparatus of claim 1, wherein said first intraoral positioning device is a bite structure for contact with opposed jaw portions of said patient.

7. The apparatus of claim 2, wherein said longitudinal reference face is defined by a longitudinal ridge extending transversely to said vertical reference face for contact with the inner sides of both of said patient's feet.

8. The apparatus of claim 7, wherein said ridge also serves as a rail means for a movable vertical plate suitable to contact both of said patient's heels.

9. The apparatus of claim 1, wherein said carriage means comprises a self-positioning control provided in the field of vision of said patient and including a cross-web means.

10. The apparatus of claim 1, wherein said carriage means further includes at least one stop means for contact with a sternal and/or clavicular body portion of said patient.

11. The apparatus of claim 1, wherein said vertical reference face of said foot positioning means includes pressure-sensitive portions for indicating a contact with said patient's toes.

12. The apparatus of claim 1, wherein said intraoral positioning device includes a bite structure having a recessed curved surface for contact with a toothless upper jaw portion, said surface being defined by a first apex.

13. The apparatus of claim 12, wherein said bite structure includes a recess portion at its lower side defined by a second apex for contact with a lower jaw portion, said second apex being closer to said axis of said column than said first apex.

14. The apparatus of claim 1, wherein said patient has a plane of mastication, said head positioning means are arranged to position and maintain said patient's plane of mastication in an essentially horizontal orientation when said longitudinal body axis is in said inclined position so as to cause a substantial elongation of the cervical vertebra.

15. In the method of taking an orthoradial panoramic tomograph of a head region of a human patient in an erect position by means of an apparatus having:
   (a) a radiation source for predetermined motion relative to a point of reference;

(b) a cassette means for selective exposure of an X-ray sensitive surface to radiation from said source, said cassette means also being arranged for predetermined motion relative to said point of reference;
(c) a support means for movingly holding said radiation means and said cassette means relative to said point of reference;
(d) a head positioning means including an intraoral positioning device and an extraoral positioning device for placing said patient's head relative to said point of reference;
(e) a carriage means connected with said support means and including a grip means;
(f) a substantially vertical column means for slidingly holding said carriage means in a vertically defined position and having a vertical axis distanced from said point of reference;

the improvement consisting essentially in causing said patient to manually engage said grip while his longitudinal body axis is maintained at an angle ($\alpha$) of from about 15° to about 25° relative to said vertical column axis to cause a substantially isotonic strain of the patient's brachial and dorsal muscles while taking a first tomograph; recording any variables of said first tomograph, and producing at least one congruent sequential tomograph of said patient under essentially identical conditions.

16. The method of claim 15, wherein said patient has a plane of mastication and a cervical vertebra, said head positioning means is arranged to maintain said patient's plane of mastication in an essentially horizontal orientation when said longitudinal body axis is maintained at said angle so as to cause a substantial elongation of said patient's cervical vertebra.

* * * * *